(12) United States Patent
Bassett et al.

(10) Patent No.: US 9,744,008 B2
(45) Date of Patent: Aug. 29, 2017

(54) SURGICAL TOOL WITH FLEXIBLE SHAFT (71) Applicant: Zimmer Dental, Inc., Carlsbad, CA (US)

(72) Inventors: Jeffrey Bassett, Vista, CA (US); Michael Scott Collins, San Marcos, CA (US)

(73) Assignee: ZIMMER DENTAL, INC., Carlsbad, CA (US)

( * ) Notice: Subject to any disclaimer, the term of this patent is extended or adjusted under 35 U.S.C. 154(b) by 573 days.

(21) Appl. No.: 14/270,856

(22) Filed: May 6, 2014

(65) Prior Publication Data

US 2014/0329197 A1 Nov. 6, 2014

Related U.S. Application Data

(60) Provisional application No. 61/819,908, filed on May 6, 2013.

(51) Int. Cl.
| | |
|---|---|
| *A61C 3/00* | (2006.01) |
| *A61C 8/00* | (2006.01) |
| *A61C 1/18* | (2006.01) |

(52) U.S. Cl.
CPC .............. *A61C 8/0092* (2013.01); *A61C 1/18* (2013.01); *A61C 8/006* (2013.01); *A61C 8/0018* (2013.01); *A61C 8/0024* (2013.01); *A61C 8/0068* (2013.01)

(58) Field of Classification Search
CPC ..... A61C 8/0018; A61C 8/0024; A61C 8/006; A61C 8/0068; A61C 8/0092; A61C 1/18
USPC ...................... 433/172–176, 72–76
See application file for complete search history.

(56) References Cited

U.S. PATENT DOCUMENTS

| | | | |
|---|---|---|---|
| 5,488,761 A | 2/1996 | Leone | |
| 6,447,518 B1 | 9/2002 | Krause et al. | |
| 6,551,321 B1 | 4/2003 | Burkinshaw et al. | |
| 7,846,162 B2 | 12/2010 | Nelson et al. | |
| 7,909,825 B2 | 3/2011 | Saravia et al. | |
| 7,914,533 B2 | 3/2011 | Nelson et al. | |
| 7,942,875 B2 | 5/2011 | Nelson et al. | |
| 8,287,539 B2 | 10/2012 | Nelson et al. | |
| 8,287,541 B2 | 10/2012 | Nelson et al. | |
| 9,039,415 B2* | 5/2015 | Streff ................... | A61C 8/0048 433/173 |
| 2003/0124488 A1* | 7/2003 | Gittleman ............ | A61C 8/0033 433/173 |
| 2006/0264950 A1 | 11/2006 | Nelson et al. | |

(Continued)

FOREIGN PATENT DOCUMENTS

| | | |
|---|---|---|
| EP | 1150612 A1 | 11/2001 |
| WO | WO-2007014355 A2 | 2/2007 |

*Primary Examiner* — Yogesh Patel
(74) *Attorney, Agent, or Firm* — Schwegman Lundberg & Woessner, P.A.

(57) ABSTRACT

An implant system can include a first rotatable flexible shaft comprising a biocompatible material and configured to be used as an implant for placement in the human body, the implant including an implant driving element positioned at a proximal end; a second rotatable flexible shaft including a cutting drill positioned at a distal end and a drill driving element positioned at a proximal end; and a surgical tool capable of being connected, in the alternative, to the drill driving element for forming a recessed surgical site and to the implant driving element for placing the implant in the recessed surgical site.

11 Claims, 8 Drawing Sheets

(56) References Cited

U.S. PATENT DOCUMENTS

| | | |
|---|---|---|
| 2006/0264951 A1 | 11/2006 | Nelson et al. |
| 2006/0264952 A1 | 11/2006 | Nelson et al. |
| 2007/0233105 A1 | 10/2007 | Nelson et al. |
| 2008/0132896 A1 | 6/2008 | Bowen et al. |
| 2008/0140078 A1 | 6/2008 | Nelson et al. |
| 2008/0161805 A1 | 7/2008 | Saravia et al. |
| 2008/0188854 A1* | 8/2008 | Moser ................ A61B 17/0401 606/80 |
| 2009/0018542 A1 | 1/2009 | Saravia et al. |
| 2010/0023010 A1 | 1/2010 | Nelson et al. |
| 2011/0071356 A1* | 3/2011 | Edwards .......... A61B 17/32002 600/142 |
| 2011/0087227 A1 | 4/2011 | Mazur et al. |
| 2011/0144645 A1 | 6/2011 | Saravia et al. |
| 2011/0183291 A1 | 7/2011 | Malo Carvalho et al. |
| 2011/0282346 A1 | 11/2011 | Pham et al. |
| 2011/0319896 A1 | 12/2011 | Papenfuss et al. |
| 2012/0029635 A1* | 2/2012 | Schoenhoeffer .......... A61F 2/44 623/17.11 |
| 2012/0239038 A1 | 9/2012 | Saravia et al. |
| 2012/0253186 A1 | 10/2012 | Simpson et al. |
| 2013/0012942 A1 | 1/2013 | Nelson et al. |
| 2013/0035598 A1 | 2/2013 | Whitman |
| 2016/0081772 A1* | 3/2016 | Schweiger ........... A61C 8/0048 433/173 |

* cited by examiner

SURGICAL TOOL WITH FLEXIBLE SHAFT

CLAIM OF PRIORITY

This application claims the benefit of U.S. Provisional Patent Application Ser. No. 61/819,908, filed on May 6, 2013, the benefit of priority of which is claimed hereby, and which is incorporated by reference herein in its entirety.

TECHNICAL FIELD

The present disclosure relates to surgical tools/instruments, and more specifically, to dental tools.

BACKGROUND

In surgical applications, access to critical areas can often be difficult due to physical anatomy and sensitivity of a surgical location. In many surgeries, space can be limited and it may be impossible to approach the surgical area directly. Visual access can also be limited. In dental surgical applications, for example in dental implant surgery, components such as screws can be extremely small, with diameters under 1.25 mm (0.049"). The installation of such screws may be necessary in a posterior oral region where access, light, and space can be extremely limited. Existing flexible shaft technology, such as that described in U.S. Pat. No. 6,447,518 contemplates the use of a cannulated flexible shaft. In view of the limitations on space and direct access in an oral region, there exists a need for flexible dental instruments and implants.

Overview

The present inventors have recognized a need for a flexible dental implant. A flexible dental implant can follow or provide a pathway around sensitive areas such as a sinus cavity. A flexible dental implant can allow a surgeon to use areas of good bone mass such as the zygomatic arch region, that can be difficult to reach with a conventional dental implant. There also exists a need for surgical tools or surgical instruments (both defined under the term surgical tools) in various applications having a flexible shaft that can, in some examples, be located within a rigid, semi-flexible, flexible or partially flexible outer tube. The outer tube can be angled or have the ability to change angulation. The flexible shaft can be cannulated or non-cannulated. The outer tube and/or the cannula of the flexible shaft can provide space for electrical wiring; fiber optic wiring; tubes for liquid or semi-liquid removal, installation or circulation; and/or bearings for increasing longevity of moving parts. The inner structures of the tube and flexible shaft can be sealed from the anatomical environment. Sealing can protect moving parts, such as bearings, and inhibit contamination. The outer tube can provide a stationary locator to measure movement of the inner flexible shaft along the longitudinal axis of the tube. Several examples in accordance with the present disclosure are set forth below:

1. Flexible Implant

Some portions of the skeletal anatomy have bone shapes that include complex features with curved surfaces and varied anatomical structures intertwined with bones. One such area is the zygomatic arch region of the human skull. In order to provide bone anchors in complex areas such as in the zygomatic arch region, a curved implant can be provided. The implant can have a flexible shaft and a threaded cutting flute at an apical end of the shaft. The flexible shaft implant can be installed with or without the use of an outer guide tube. Torque from a manual or motorized input can be delivered down the flexible shaft, and the implant can be drawn into the implant site as the apical end is rotated. The curved implant can be steerable or self-steering. A cutting tip can be provided that can be steerable toward hard bone structure and away from softer features such as the sinus cavities or the eye cavity. The tip of the implant can be steerable by means of wires or cables controllable at the proximal end of the implant. The device can use guided surgery as outlined above and can have fiber optic and/or electronic features to aid in placement and guidance. The flexible shaft can bend around anatomical features such as the sinus cavities in the head. Such an implant is not limited to the zygomatic arch region, but can have applications in other regions of the anatomy. The proximal end of the flexible implant can have any abutment or anchor attaching members known to those skilled in the art. In an example the proximal end of the flexible implant can have a conical connection and internal threading to receive a fastener. The distal end of the flexible implant can be configured to anchor to bone. In an example the distal end can be configured of a porous or semi-porous material designed to allow the osseointergration of bone. In an example the distal end can be threaded to provide a means to anchor the implant into the bone. In an example the distal end can have anchoring members such as protrusions, pins or shapes which aid bone anchoring and attachment. The implant can be manufactured of any biocompatible material, such as titanium. Additionally, the device can have any one or any combination of the features outlined above.

2. Flexible Drilling Apparatus

The apparatus outlined above can be attached to a drill for use in dental implant osteotomies, bone blocks, sinus lifts, bone tunneling, minimally invasive surgical techniques, and cranio-maxillofacial plates and screws. A drill with a flexible shaft drive and an outer tube with a fixed or adjustable angle can also be used in implant sites that are curved, for example a zygomatic implant. The angled drill tip can be steerable through the use of control mechanisms such as control wires in a flexible guide tube. Curved implant holes can be used in applications using two tilted implants and two or more vertically placed implants such as the Zimmer Dental Revitalize™ products. In these types of restoration providing solid bone for anchoring might be difficult. The tool tip on the flexible drill can be replaced with any cutting device such as a rotary file, end mill or burr. The tool can be applied to bone profiling applications and could be used with any tool benefiting from rotary motion.

The steerable drill tip can be computer guided by inputting computerized tomography scan or x-ray data from a surgical site into a computer processor that can aid or control drilling. A guided drill processor can map out a drilling route and either steer the drill tip automatically or warn a surgeon if he was veering off a mapped drilling pathway.

The drill tip can optionally have a depth control feature. Depth control can be accomplished mechanically by measuring and controlling advancement of the flexible shaft relative to the outer tube. The depth control could be controlled electronically through the use of potentiometers, Hall Effect sensors or fiber optic laser measuring applications.

The flexible shaft can be cannulated and liquids can be pumped in or out from the tip of the flexible shaft tool. For any drilling application in living bone, cooling can be very important as temperatures as low as 47° C. have been shown to cause bone cell death. The drill tip can be irrigated to reduce heat buildup and remove debris. The cooling system can be a closed system. A closed cooling system can prevent contaminants from the oral site from entering small passages in a drill or other tool and migrating to the inner portions of the outer tube or flexible shaft. In a closed system, the tool can have passages for the flow of coolant. The tool material can provide good heat exchange between the cutting area and the coolant. The coolant can be refrigerated for added cooling performance. Furthermore, in the closed system, the coolant and coolant passages can be designed such that they would never come into contact with bacteria or other contaminants from the oral or anatomical site.

A flexible drilling apparatus can have all the features outlined above such as light, video, camera and computer guided features. The angle of the outer tube can be controllable manually, by automated controls such as solenoids or by computer, and this can be accomplished over variable curve radii and in more than one location on the guide tube.

The outer guide tube can have two or more portions that are bendable. The bendable regions of the outer guide tube can be configured similar to a "straw" with a concertina hinge or a reinforced hose section with a shape memory. The tip of the flexible drill can be steerable and the outer guide tube can be flexible. This type of arrangement can drill a complex hole. The drill can be manufactured to draw into the drilled material during use, and the proximal end of the flexible apparatus can follow the steerable drill tip. The drill can have a manual or automatic feed control.

3. Cannulated Implant and Drills

A multi-function tool can be provided that can act as a driver, a drill or a cutting tool. The tool can have an outer guide tube and an inner cannulated flexible shaft. The tool can be used for installing/removing implants, installing/removing fasteners, drilling holes, or making surgical cuts. In many surgical applications it can be beneficial to use small wires to penetrate anatomical structures and guide larger instruments to a particular surgical site. The wires can be guided by x-ray, computer tomography or other suitable imaging technologies. The wire pathway may not be a straight line and may be required to circumvent structures. The guide wire can provide alignment and accuracy for later surgical procedures such as drilling, cutting or implant installation. A cannulated implant or drill with a flexible shaft can follow a guide wire. The tool can have any one or any combination of the features outlined above.

4. Flexible Driver Features

The present disclosure can have applications in any field where access is difficult and can be improved by use of a driving tool that can include a rotating distal member within an angled outer guide tube. A flexible shaft can be located inside of the outer guide tube. The flexible shaft can be rotated within the outer guide tube. The flexible shaft can include a tool attachment member on the distal end, such as a latch lock type connection interface. This connection can be used to attach drivers for installing threaded implants or screws for abutments, bone blocks, bone graft membranes, cranio/maxilla/facial applications. The driver can be manually driven by a knob or handle on the proximal end, or attached to a motor drive for increased torque, accuracy and/or control. In an example, a manual handle can be mounted on a proximal end of a flexible shaft. The handle can be removable and the proximal end can alternately be attachable to a motor drive. In an example, the manual handle can be removed and an adaptor can be used to connect the tool to existing motorized tools such as a dental contra angle.

The flexible driver can have an adjustable torque control. The torque control can be a mechanical torque control with a deflecting beam or a click type with a ball and spring. The torque control can be electrical by means of a strain gage attached to a torsion rod or through the use of direct torque control of an electrical motor drive.

The flexible driver can be supplied with electricity and/or fiber optics at the distal end through the interior lumen of the flexible shaft, the interior lumen of the outer tube or on another portion of the outer tube. Electrical connections for a moving shaft can be made through any known slip ring or rotary electrical interface. Fiber optic rotary connections can be made with a fiber optic rotary joint. Electrical or optical power at the distal end of the flexible driver can power light, camera, borescope, video or other such applications. Camera/video applications can be magnified using optics and relayed to a computer/video screen at a nearby or remote location. Signals can be transmitted via wired or wireless connections. Controls for the motorized power can be hand or foot operated.

The flexible driver can optionally have a depth control feature. Depth control can be accomplished mechanically by measuring and controlling advancement of the flexible shaft relative to the outer tube. A spring loaded plunger can engage an implant or screw and move as the implant or screw moves away from the outer guide tube. The depth control can be controlled electronically through the use of sensors such as potentiometers, Hall Effect sensors or fiber optic laser measuring applications. Depth control of an advancing implant or screw can be controlled by counting turns of the rotatable shaft and relating the turns to a thread pitch of a fastener or displacement of a driven item (e.g. a fastener). Turn counting can be accomplished manually, mechanically or electronically. Materials for the outer guide tube and the flexible shaft can include metals, metal alloys, polymers, or carbon fibers.

5. Multi-Function Tool

A multifunction tool with a flexible shaft and a rotating tip can be configured as a driving tool, a drilling tool or a cutting tool. The multifunction tool can have any one or any combination of the features outlined above. The tool connection can be a quick release configuration providing a maximum efficiency for the operator.

6. Bone Harvesting Tool

Bone harvesting for creating a bone graft can require access to a difficult to reach portion of the anatomy with restricted space available for a procedure. A flexible shaft cutting tool with a longitudinal guide tube having an adjustable angular portion can be used under such circumstances. The flexible shaft cutting tool can increase efficiency, provide a minimally invasive surgery, and improve healing time. Areas of the anatomy that such a tool can be used include, but are not limited to, the ramus of the mandible, the iliac crest, and the chin. The flexible shaft cutting tool can have any one or any combination of the features outlined above.

7. Bone Shaving Tool

The tool can be configured to reach into areas of the jaw such as the mandibular symphysis (chin area) or Coronoid process of the mandible to harvest block or particulate autologous grafting material. The flexibility of the tool can allow for a much less invasive procedure. A cutting or drilling tool with increased flexibility and the ability to be configured in variable angles and/or multiple angles can be provided for this procedure. The tool can have any one or any combination of the features outlined above.

8. Soft Tissue Harvesting

Soft tissue harvesting may require access into portions of a cavity that have limited space or are difficult to reach. A cutting tool can be provided with a flexible shaft configured to rotate within an outer guide tube. One or more cutting tips can be provided for attachment to a distal end of the flexible shaft, such as in a surgical kit form. As described above, the guide tube can have one or more angles, the angular region can be adjustable, and the depths of the cutting tip can be adjustable. Such a tool can be used for palletal graft harvesting (free gingival grafts), subepithelial connective tissue grafts, and lateral pedicle grafts, as well as alternate uses. Additionally, the cutting tool can have any one or any combination of the features outlined above.

9. Subantral Graft or Sinus Lift Instrument

In a sinus lift procedure, the bone underneath the sinus membrane must be penetrated. A surgeon must be careful not to damage the sinus membrane when the bone penetration is being performed. A cutting or drilling tool with increased flexibility and the ability to be configured in variable angles and/or multiple angles can be provided for this procedure. The tool can have any one or any combination of the features outlined above. The tool can be configured to cut through the sinus floor, sparing the Schnideran membrane. The cannulated center section could then be used to transport and pack bone grafting material underneath the membrane raising the floor of the sinus cavity. In the event of membrane damage the tool can be equipped with pinchers to deliver a membrane grating material.

10. Delivering Biologic Materials Thru Tube/Cannulae/Flexible Shaft

Many surgical applications require the delivery or removal of liquid, semi-liquid or paste-like substances. With the advent of minimally invasive surgery, some surgical sites are not readily accessed by routine measures. Some surgical sites have limited space and are difficult to reach, such as locations in the oral or sinus cavities. A tool can be provided that can access a site through a curved pathway or an angled guide tube. The tool can include a flexible shaft disposed within a guide tube that can be aligned internally or externally with an impermeable membrane. The tool can be used to pump material into or out of a surgical site. Such materials can include, for example, bone graft materials, bone morphogenetic proteins (BMPs), growth factors, antibiotics, or the like. Additionally, the tool can have any one or any combination of the features outlined above.

To better illustrate the surgical tool systems and methods disclosed herein, a non-limiting list of examples is provided here:

In Example 1, an implant system can comprise: a first rotatable flexible shaft comprising a biocompatible material and configured to be used as an implant for placement in the human body, the implant including an implant driving element positioned at a proximal end; a second rotatable flexible shaft including a cutting drill positioned at a distal end and a drill driving element positioned at a proximal end; and a surgical tool capable of being connected, in the alternative, to the drill driving element for forming a recessed surgical site and to the implant driving element for placing the implant in the recessed surgical site.

In Example 2, the implant system of Example 1 can optionally be configured such that wherein the surgical site is formed in a zygomatic arch region of a human skull.

In Example 3, the implant system of any one or any combination of Examples 1 or 2 can optionally be configured such that the implant comprises a diameter between about 3 mm and about 6 mm and a length between about 20 mm and about 50 mm.

In Example 4, the implant system of any one or any combination of Examples 1-3 can optionally be configured such that the surgical tool is flexible.

In Example 5, the implant system of any one or any combination of Examples 1-4 can optionally be configured such that the implant driving element is configured to receive a tooth prosthetic.

In Example 6, the implant system of any one or any combination of Examples 1-5 can optionally be configured such that the surgical tool further comprises an outer guide tube including a longitudinal body extending from a proximal end to a distal end, wherein the outer guide tube includes at least one straight portion and at least one angled portion.

In Example 7, the implant system of Example 6 can optionally be configured such that the at least one angled portion is flexible.

In Example 8, the implant system of any one or any combination of Examples 6 or 7 can optionally be configured such that the surgical tool further comprises at least one of: a bearing positionable between the guide tube and the first rotatable flexible shaft or the second rotatable flexible shaft; and a seal positionable between the guide tube and the first rotatable flexible shaft or the second rotatable flexible shaft.

In Example 9, a surgical tool can comprise: an outer guide tube including a longitudinal body extending from a proximal end to a distal end, wherein the outer guide tube includes one or more angled portions; a rotatable flexible shaft member configured to be positioned within the outer guide tube, wherein the flexible shaft member includes a proximal end connection and a distal end connection; a driving device including a mating connection configured to engage with the proximal end connection; a driven element including a mating connection configured to engage with the distal end connection; and a cooling system including one or more fluid passages extending between the flexible shaft member and the driven element, wherein the cooling system is refrigerated.

In Example 10, the surgical tool of Example 9 can optionally be configured such that the driven element is at least one of a drill, a burr, a mill, a screw or an implant.

In Example 11, the surgical tool of Example 10 can optionally be configured such that the driven element is an implant, and wherein the implant is flexible.

In Example 12, the surgical tool of any one or any combination of Examples 9-11 can optionally be configured to further comprise at least one of: a bearing positioned between the flexible shaft member and the guide tube; and a seal positioned between the flexible shaft member and the guide tube.

In Example 13, the surgical tool of any one or any combination of Examples 9-12 can optionally be configured such that at least one of the flexible shaft member and the driven element is cannulated.

In Example 14, the surgical tool of any one or any combination of Examples 9-13 can optionally be configured such that at least one of the one or more angled portions are flexible.

In Example 15, the surgical tool of any one or any combination of Examples 9-14 can optionally be configured to further comprise an adjustable torque control device configured to be operably coupled to the flexible shaft member.

In Example 16, the surgical tool of any one or any combination of Examples 9-15 can optionally be configured to further comprise a depth control member configured for measuring a distance between the distal end of the outer guide tube and a distal end of the driven element.

In Example 17, the surgical tool of any one or any combination of Examples 9-16 can optionally be configured to further comprise an optical sensing device configured to transmit images from the optical sensing device to a display screen.

In Example 18, the surgical tool of any one or any combination of Examples 9-17 can optionally be configured to further comprise an irrigation system.

In Example 19, a dental implant can comprise: a rotatable flexible shaft comprising a biocompatible material and having a distal end and a proximal end, the distal end configured as a cutting tip and the proximal end configured to be driven by a driving tool during insertion of the dental implant, wherein the proximal end of the rotatable flexible shaft is configured to receive a dental prosthetic after insertion of the dental implant.

In Example 20, the dental implant of claim 19 can optionally be configured such that the dental implant has a diameter in a range between about 3 mm and about 6 mm and a length in a range between about 20 mm and about 50 mm.

In Example 21, the implant system, the surgical tool, and the dental implant of any one or any combination of Examples 1-20 can optionally be configured such that all elements, operations, or other options recited are available to use or select from.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present patent application relates to a surgical tool assembly having a flexible shaft. As outlined in the OVERVIEW section and described in further detail below, the surgical tool assembly can include numerous configurations. These configurations are exemplary in nature and are not intended to limit the spirit and scope of the present disclosure. Thus, numerous other configurations are also contemplated.

Figure 1:
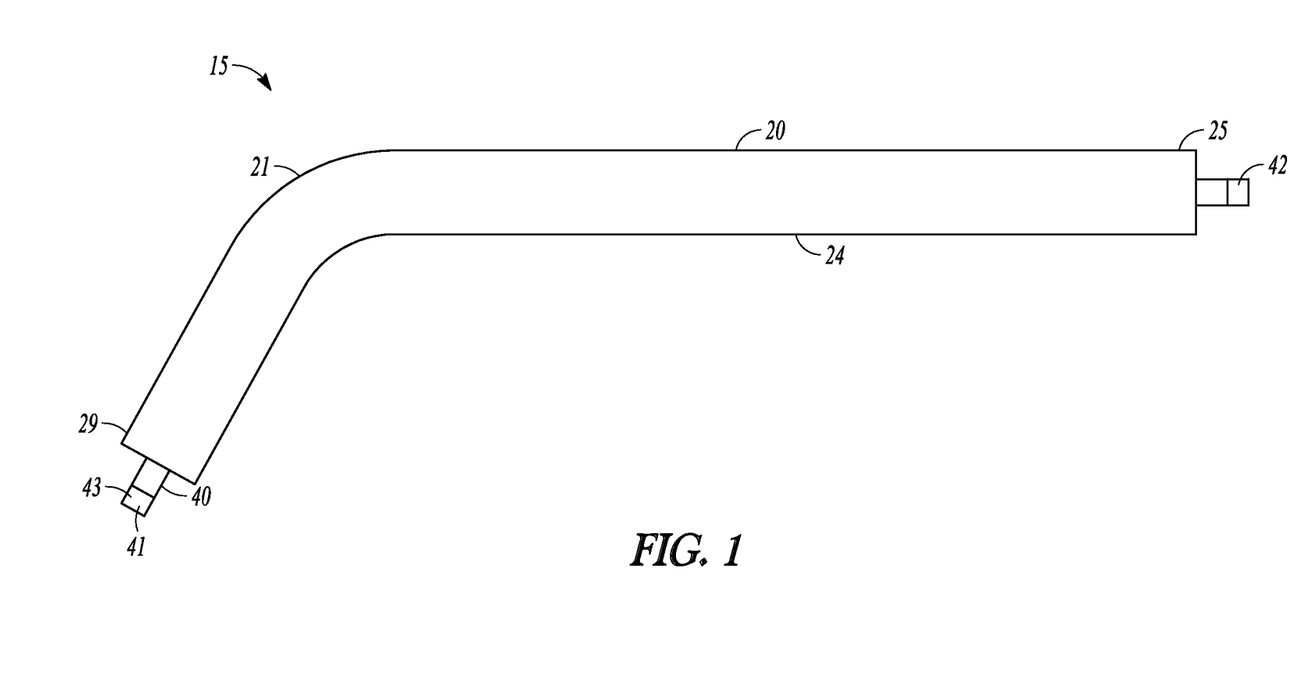
FIG. 1 illustrates an outer guide tube and flexible shaft assembly, in accordance with at least one example of the present disclosure.

FIG. 1 is a side view of a surgical tool 15 in accordance with at least one example of the present disclosure. As illustrated in FIG. 1, the surgical tool 15 can include an outer guide tube 20 and a flexible shaft member 40. The outer guide tube 20 can have a longitudinal body 24 extending from a tube proximal end 25 to a tube distal end 29. The outer guide tube 20 can include an inner lumen 27 (see FIG. 3) through which the flexible shaft member 40 can pass. The flexible shaft member 40 can be rotatable within the outer guide tube 20. The flexible shaft member 40 can include a shaft proximal end 42 and a shaft distal end 41. The flexible shaft member 40 can be cannulated throughout its length. The shaft distal end 41 can include a mating device connection 43. The mating device connection 43 can be configured to connect a separate device such as a drill, burr, mill, or driving tool. The shaft distal end 41 can also be configured to directly act as a tool, such as a drill, burr, mill, or driving tool. The shaft proximal end 42 can be configured to connect to one or more driving devices, such as a manual handle or a motor device, which can perform one or more of rotating, advancing, or retracting the flexible shaft member 40. The connections at the ends 41, 42 can be configured as hex, square, collet, right angle latch, latching, taper, locking, threaded, or any type of available connecting means known to those skilled in the art. The outer guide tube 20 can have a bend section 21 which can allow the longitudinal body 24 to be configured in various angles and positions to suit a particular surgical procedure.

Figure 2:
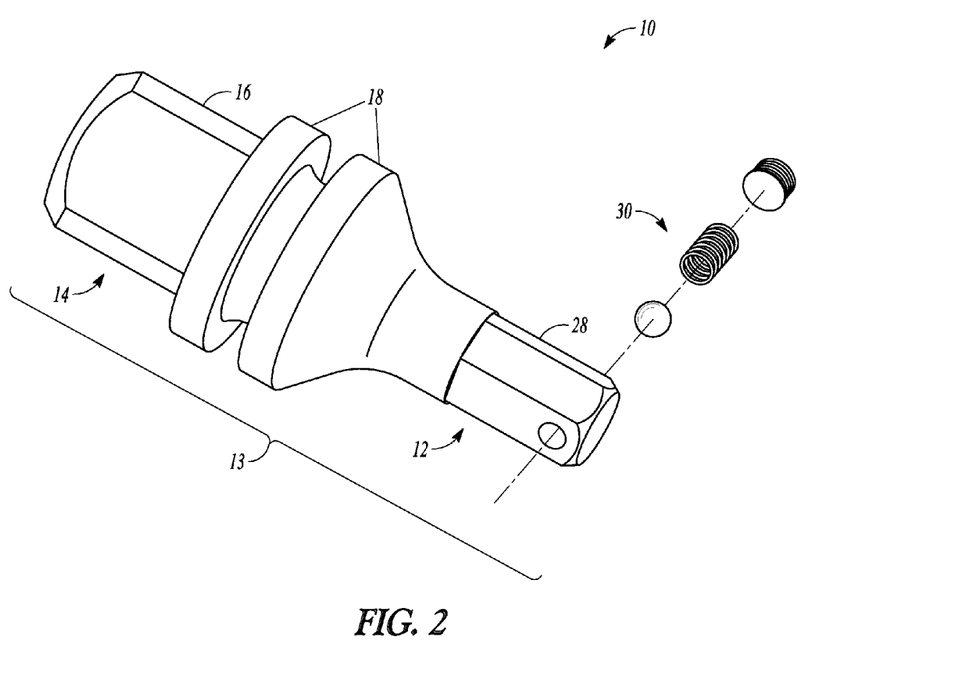
FIG. 2 illustrates a driver for an implant or tool, in accordance with at least one example of the present disclosure.

FIG. 2 is a perspective view of a driving tool 10 that can be used with a surgical tool in accordance with at least one example of the present disclosure. The drive tool 10 can generally include a drive tool body 13 which can be an elongated body or shaft that can extend from a distal end or device engaging end 12 to a drive tool proximal end 14. The drive tool 10 can be formed of various materials known to those skilled in the art, such as titanium, steel, polymer or composites. The drive tool proximal end 14 can include a hexagonal projection 16 that can be adapted to connect to the shaft distal end 41 (see FIG. 1). The drive tool body 13 of the drive tool 10 can include one or more flange members 18 which can form a snap fit with a mating connection on the shaft distal end 41, such as the mating device connection 43 (see FIG. 1). The drive tool proximal end 14 can have other connection configurations known to those skilled in the art such as polygonal, square, collet, right angle latch, latching, taper, locking or threaded. The shaft distal end 41 can have a corresponding mating connection structure. The shaft proximal end 42 (see FIG. 1) can include connection means that can be similar to the connections contemplated for the driving tool 10 as well as connections to a motorized driving device.

The distal end 12 can be configured as, for example, a driving tool, a drill, a burr, a mill or a cutting device. The distal end 12 can have a connecting means, such as a spring loaded ball assembly 30 that can provide a connection mechanism with a mating feature in a component such as an implant or a screw. All connecting means can be cannulated. Connections can have electronic or fiber optic elements associated with the connection. The drive tool distal end 12 can have a hexagonal shape 28 or have other connection configurations known to those skilled in the art such as polygonal, square, collet, right angle latch, latching, taper, locking or threaded. Connections can include sealing means configured to allow for the flow of liquids through a cannulated connection without any substantial leakage. Seals can include, for example, o-rings, gaskets, or pistons, and can be made from any suitable material such as rubber, polymer, Teflon, or metal.

Figure 3:
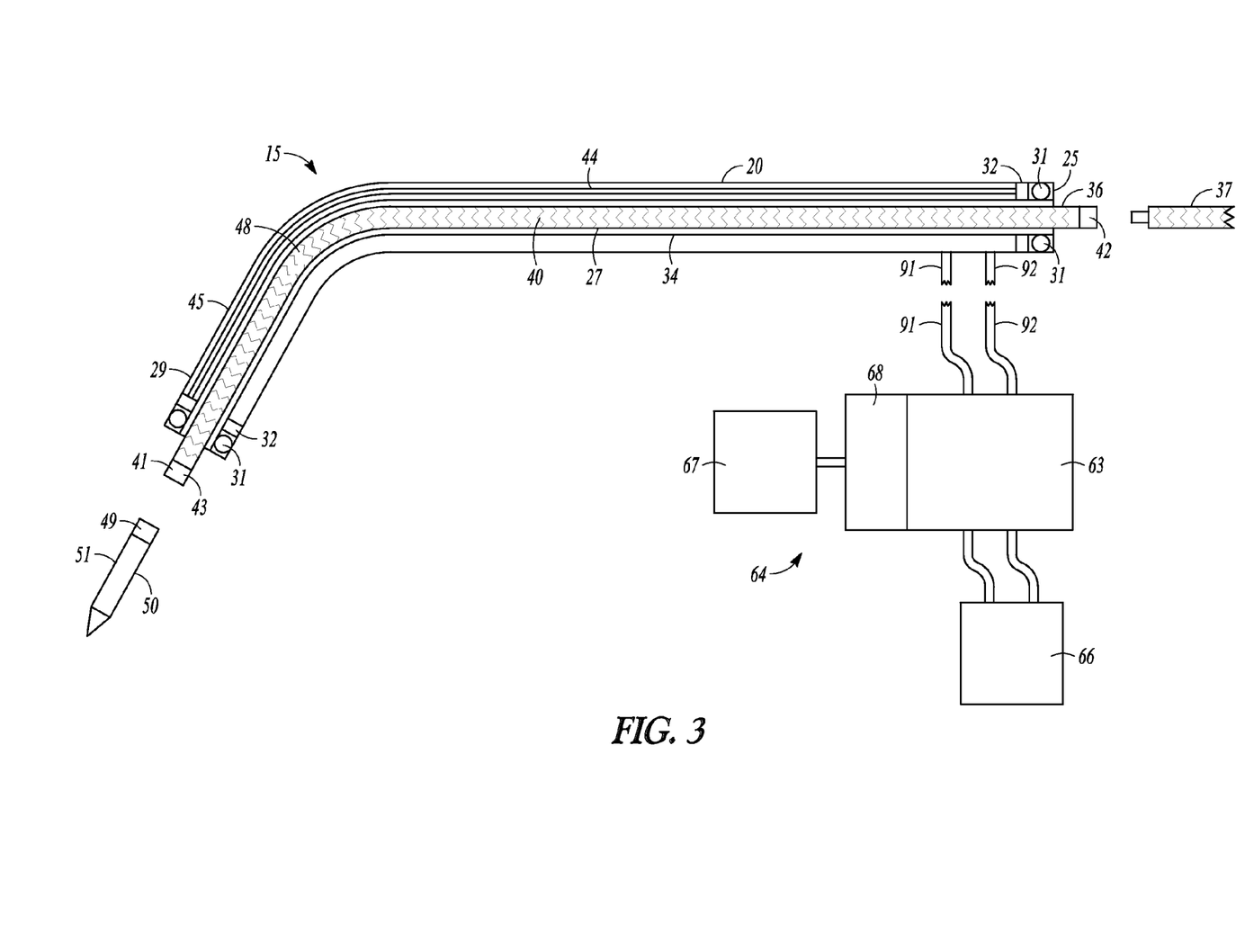
FIG. 3 illustrates a partial cross-section of an outer guide tube, in accordance with at least one example of the present disclosure.

FIG. 3 illustrates a partial cross-sectional view of the surgical tool 15 in accordance with at least one example of the present disclosure. An inner lumen 27 can extend from the tube proximal end 25 to the tube distal end 29. As shown in FIG. 3, the flexible shaft member 40 can extend within the inner lumen 27. The flexible shaft member 40 can be configured in any suitable manner such as a wire, a coil or a jointed structure. In an example, the flexible shaft member 40 can be configured in small interlocking sections 48 which can allow the shaft to transmit torque and flex. The flexible shaft member 40 can be cannulated, and can include a sheath 34 which can aid the transmission of liquids or semi-solids without leakage. The sheath 34 can be located on the outside or inside of the flexible shaft member 40.

The flexible shaft member 40 can be advanceable or retractable within the outer guide tube 20. The advancement/retraction of the flexible shaft member 40 can be controlled by any suitable means, such as manually or via a motor. The advancement of the flexible shaft member 40 can be automatically controlled so that a feed rate of the advancement can be set to a desired value. The flexible shaft member 40 can include resettable feed stops so that a total feed amount of advancement can be set.

Figure 4A:
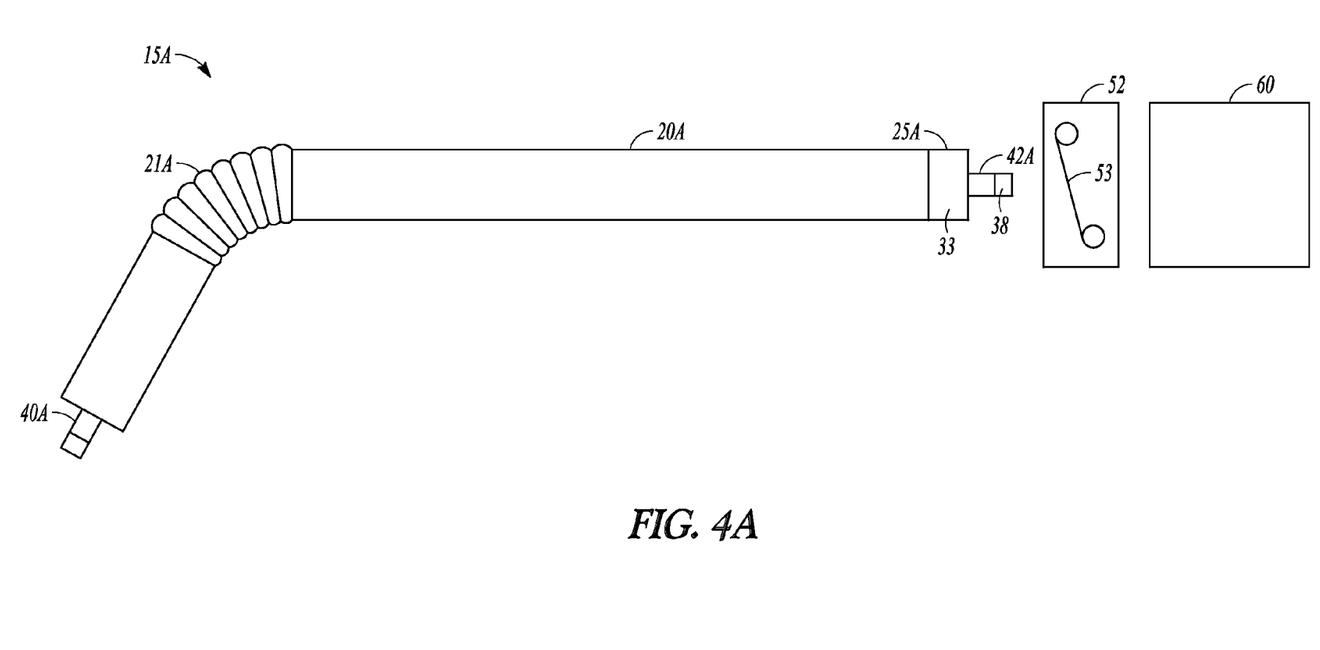
FIG. 4A illustrates an outer guide tube with an adjustable bend, in accordance with at least one example of the present disclosure.

The outer guide tube 20 can include one or more seals 32 at the ends 29, 25 which can prevent materials from entering or exiting the lumen 27. The outer guide tube 20 can include one or more bearings 31 at the ends 29, 25 or at other advantageous locations that can act to prolong the life of moving parts and/or allow increased rotational speeds. As further illustrated in FIG. 3, the flexible shaft member 40 can be configured as a flexible implant 36. The flexible shaft member 40 or the flexible implant 36 can be attached to one or more modular members, such as a flexible driving member 37 that allow the shaft to be extended to a desired length. The shaft proximal end 42 can be connected to the flexible driving member 37, a manually driven handle 52, or a motorized unit 60 (see FIG. 4). The outer guide tube 20 can include cabling 44 which can provide electrical wires and/or optical fibers to connect sensors, lights, cameras etc. at the tube distal end 29, which can be controlled near the tube proximal end 25. Cabling 44 can be protected from the rotation of the flexible shaft member 40 by any means known to those skilled in the art, such as by including in a separate lumen or tube.

In an example, the flexible implant 36 can be connected to a flexible driving member 37 operably coupled to or formed integral with the flexible shaft member 40. The connected members can be loaded into a guide tube 20. The flexible implant 36 can have cutting means at its tip as well as one or more auxiliary features such as steering, lights, cameras, irrigation, anchors or the like. The flexible implant 36 can have the majority of its length inside of and supported by the guide tube 20 as it is initially driven into a pre-drilled pilot hole in a bone. The length of the flexible implant 36 can be preselected to match a preselected implant route in an anatomy. As the implant advances into the bone material the modular connection between the flexible implant 36 and the flexible driving member 37 can eventually exit the confines of the guide tube 20 and then can be driven to a final depth in the bone. The flexible driving member 37 can be disconnected from the flexible implant 36 and the flexible implant 36 can remain seated in the bone.

In an example, the surgical tool 15 can be used to control a driven element 50 such as a driving tool, a burr, a saw tool, or a drill 51 as illustrated in FIG. 3. The driven element 50 can be any tool adapted for a particular procedure which can include cutting, suctioning, irrigating, driving, image or data gathering, impacting or drilling. The driven element 50 can be adapted to perform any one or any combination of these procedures. A driven element connection 49 can securably connect with the mating device connection 43 at the shaft distal end 41. The outer guide tube 20 can have a substantially straight portion 45 near the tube distal end 29. This straight portion can be utilized for the retraction of a tool with a non-flexible shaft, such as at least a portion of the length of the drill 51. The drill 51 can be retracted into the straight portion 45 to provide increased stability as a drilling procedure is initiated. The flexible shaft member 40 can be connected to the drill 51 by means of the mating device connection 43 at the shaft distal end 41 and the driven element connection 49, which can be located at the proximal end of the drill 51. As the drill 51 performs a drilling procedure, the tip of the drill 51 can attain an increased stability as it is advanced deeper into a drilled hole. During the drilling procedure, the flexible shaft member 40 can be advanced within the outer guide tube, thereby pushing at least a portion of the drill 51 out of the straight portion 45.

The driven element 50 can be cannulated and can be configured to pump fluids into or out of a work area. In an example, if the procedure requires irrigation, fluids can be pumped from a fluid pumping system 64, down the cannulated flexible shaft member 40 and out the driven element 50. The fluid pumping system 64 can include a fluid reservoir 67 and a fluid pump 68. In an example, the flexible shaft member 40 can be used to access a surgical area that can require the introduction of bone graft material. This material can be in a paste-like form and can be pumped through the flexible shaft member 40 and out the driven element 50 configured for such a purpose. In another example, if the surgical area requires the removal of fluids, the surgical tool 15 can be configured to suction fluids. In yet another example, if a surgical location requires visual aids, such as lighting, camera, or computer aided surgery sensing, these types of devices can be incorporated into the driven element 50, and can be connected via wiring through the flexible shaft member 40 or through the use of wireless transducers. In some procedures, the driven element 50 can remain in close proximity to the tube distal end 29. In such embodiments, the tube distal end 29 can be configured to, for example, deliver or remove fluids, provide light, provide camera functions, or provide computer aided surgery functions.

As illustrated in FIG. 3, the surgical tool 15 can include a cooling system, such as a closed cooling system 63. The closed cooling system 63 can be configured to pump cooling fluid through the flexible shaft member 40 and into passages of the driven element 50. The closed cooling system 63 can provide cooling to a drill tip and keep drilled materials such as living bone at a beneficial low temperature. The cooling fluid can be refrigerated to a desired temperature in a refrigeration unit 66 connected to the closed cooling system 63 to provide even greater cooling ability. The cooling system 63 can include a fluid send line 91 and a fluid return line 92. The fluid send line 91 can transport a cooling fluid to cool the distal end of a drill, implant, and/or aid in cooling a surgical site. The fluid return line 92 can transport fluid back to the refrigeration unit 66 or other cooling device for re-cooling. Similar fluid lines can be configured for irrigation, suction, or other types of cooling systems. The driven element 50 can include temperature sensing devices which can transmit temperature information by any suitable means, such as via a wire or wirelessly.

FIG. 4A illustrates a side view of a surgical tool 15A including an outer guide tube 20A and a flexible shaft member 40A, in accordance with at least one example of the present disclosure. As in previous examples, the flexible shaft member 40A can rotate, retract, or advance within an inner lumen of the outer guide tube 20A. The outer guide tube 20A can include an adjustable bend section 21A. The adjustable bend section 21A can be configured as a concertina type hinge, a reinforced flexible hose, a modular jointed section or any other type of flexible tubular construction known to those skilled in the art. The adjustable bend section 21A can be configured with varying degrees of flexibility such that in some configurations the adjustable bend section 21A will readily retain any shape that has been formed, while in other configurations the adjustable bend section can have a dynamic flexibility that changes more easily. The adjustable bend section 21A can be configured for adjustment manually, mechanically, or automatically. A mechanical configuration can include a series of control rods, control wires, or control cables to allow an operator to manipulate the angle or direction of the adjustable bend section 21A from a proximal end 25A of the surgical tool 15A. The adjustable bend section 21A can include a series of hydraulically or electronically controlled solenoids which can provide an automatic control to the adjustable bend section 21A.

Figure 4B:
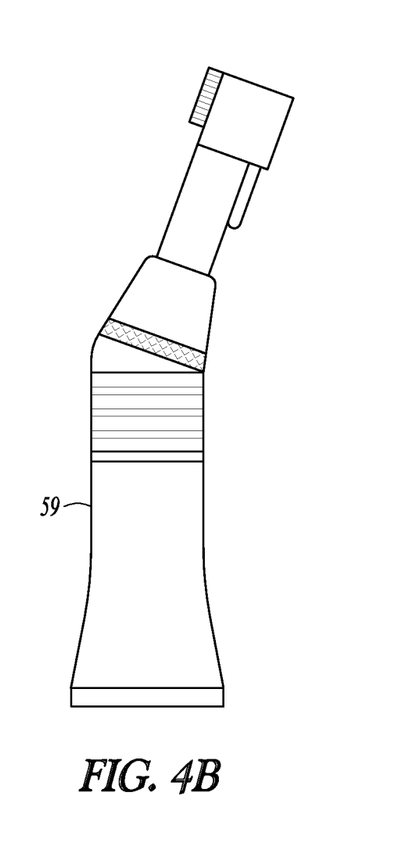
FIG. 4B illustrates a motorized device, in accordance with at least one example of the present disclosure.
Figure 4C:
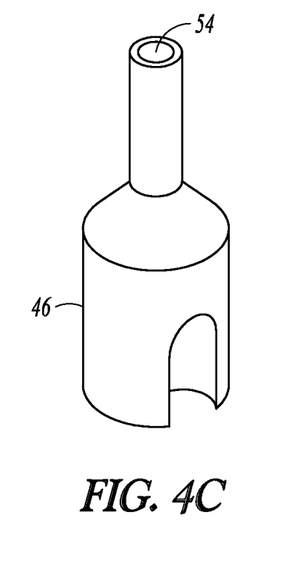
FIG. 4C illustrates an adaptor, in accordance with at least one example of the present disclosure.

The shaft proximal end 42A can include a shaft proximal device connection 38. The shaft proximal device connection 38 can be configured to connect to a manually driven handle 52, a flexible driving member 37 (see FIG. 3), or a motorized unit 60. The shaft proximal device connection 38 can include any type of connection interface known to those skilled in the art such as a collet, socket, threaded, tapered, locking, latching, or gripping connection. The connection interface 38 can be configured to transmit fluids, electricity or light. FIGS. 4B-4C illustrate a motorized device and an adaptor, in accordance with at least one example of the present disclosure. Returning also to FIG. 4A, the tube proximal end 25A can have a tube connection 33 that can provide a connection interface to an adaptor 46, the handle 52, the motorized unit 60, or a holding or clamping device which can provide stability to the shaft proximal end 42A. The adaptor 46 can be configured to receive the shaft proximal end 42A in an adaptor lumen 54 and connect to a motorized device such as a contra angle 59 (not shown in same size scale).

The handle 52 can include a torque device 53. The torque device 53 can provide torque measuring and/or torque control of the flexible shaft member 40A. Torque measuring and control can be useful when the surgical tool 15A is used to install implants, screws, fasteners, or the like. In certain applications such devices can be extremely small and attaining the proper torque can be important. The torque control can be a mechanical torque control with a deflecting beam or a click type with a ball and spring. The torque control can be electrical by means of a strain gage attached to a torsion rod or through the use of direct torque control of an electrical motor drive. The torque can be measured by any means known to those skilled in the art. The torque device 53 can be located in the handle 52 or in another exterior unit, such as the motorized unit 60. The torque device 53 can be adjustable, settable and limitable. When a certain torque has been reached, the limitable function can stop any additional torqueing force from being delivered by the handle 52 or motorized unit 60.

Figure 5:
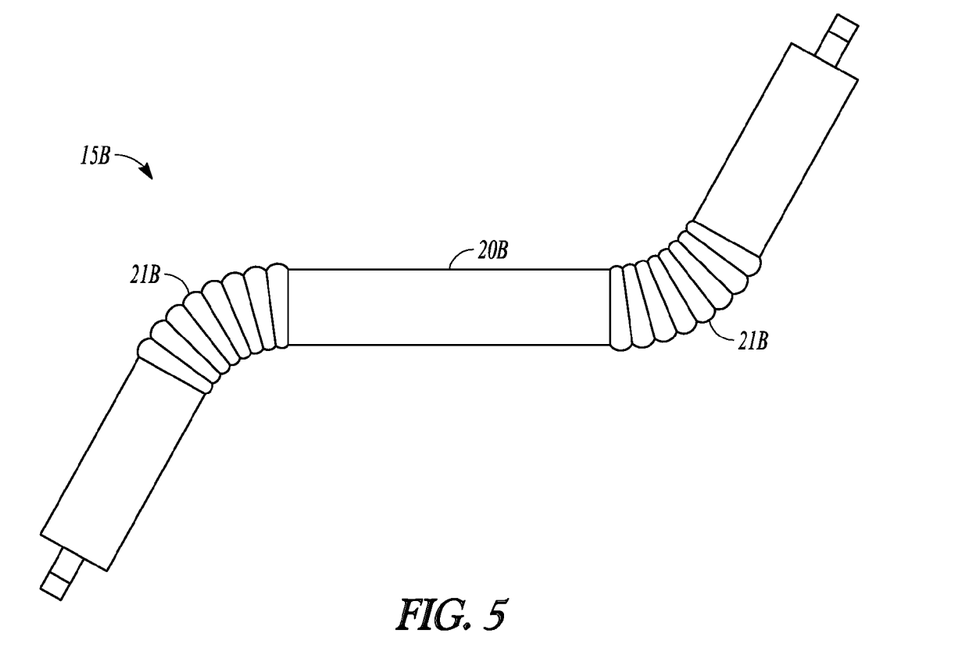
FIG. 5 illustrates an outer guide tube with multiple adjustable bends, in accordance with at least one example of the present disclosure.

FIG. 5 illustrates a surgical tool 15B having two or more adjustable bend sections 21B in a guide tube 20B, in accordance with at least one example of the present disclosure. The adjustable bend sections 21B can include any of the adjustable bend configurations disclosed above. Furthermore, each of the adjustable bend sections 21B include the same adjustable bend configuration, or at least one of the adjustable bend sections 21B can be designed with a different adjustable bend configuration.

Figure 6:
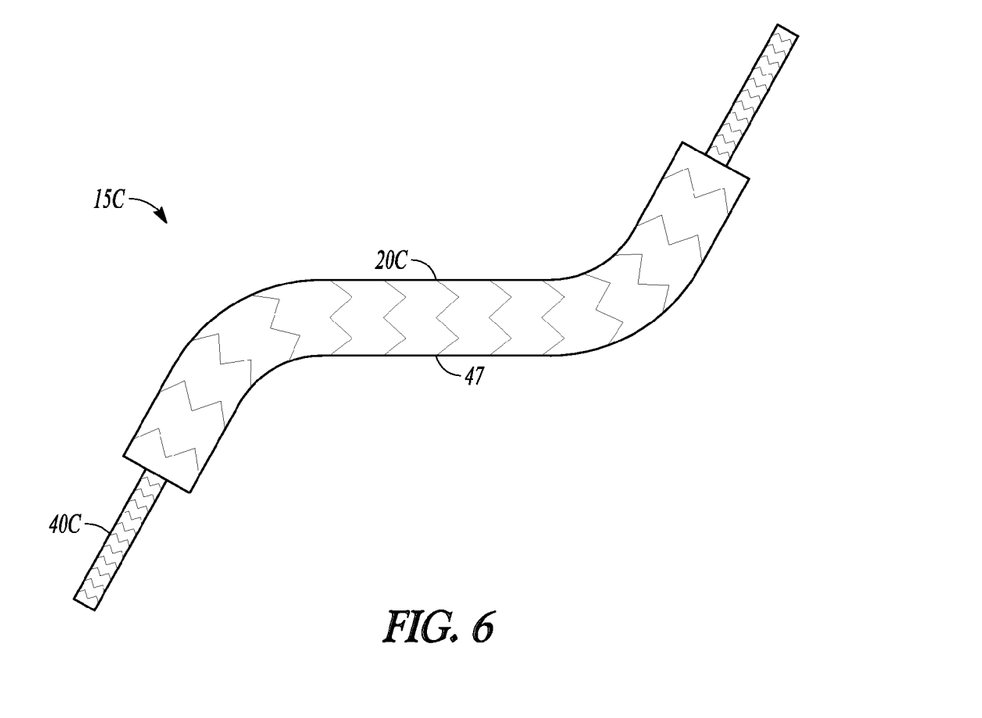
FIG. 6 illustrates a flexible shaft within a flexible outer guide tube, in accordance with at least one example of the present disclosure.

FIG. 6 illustrates a surgical tool 15C with an outer guide tube 20C having at least a portion of its length being flexible, in accordance with at least one example of the present disclosure. In an example, the entire length of the outer guide tube 20C can be flexible. As illustrated in FIG. 6, the flexible outer guide tube 20C can be configured as a series of modular interlocking units 47. The flexible outer guide tube 20C can also be configured as a reinforced hose, a coiled wire or any other suitable means for providing a flexible outer stationary member configured to receive an inner rotating flexible shaft 40C. The outer guide tube 20C, whether rigid, flexible, or partially flexible, can be supported in any part of its length by clamps or support members to aid in a surgical procedure. Furthermore, the outer guide tube 20C can have fittings adapted for such clamps support members.

Figure 7:
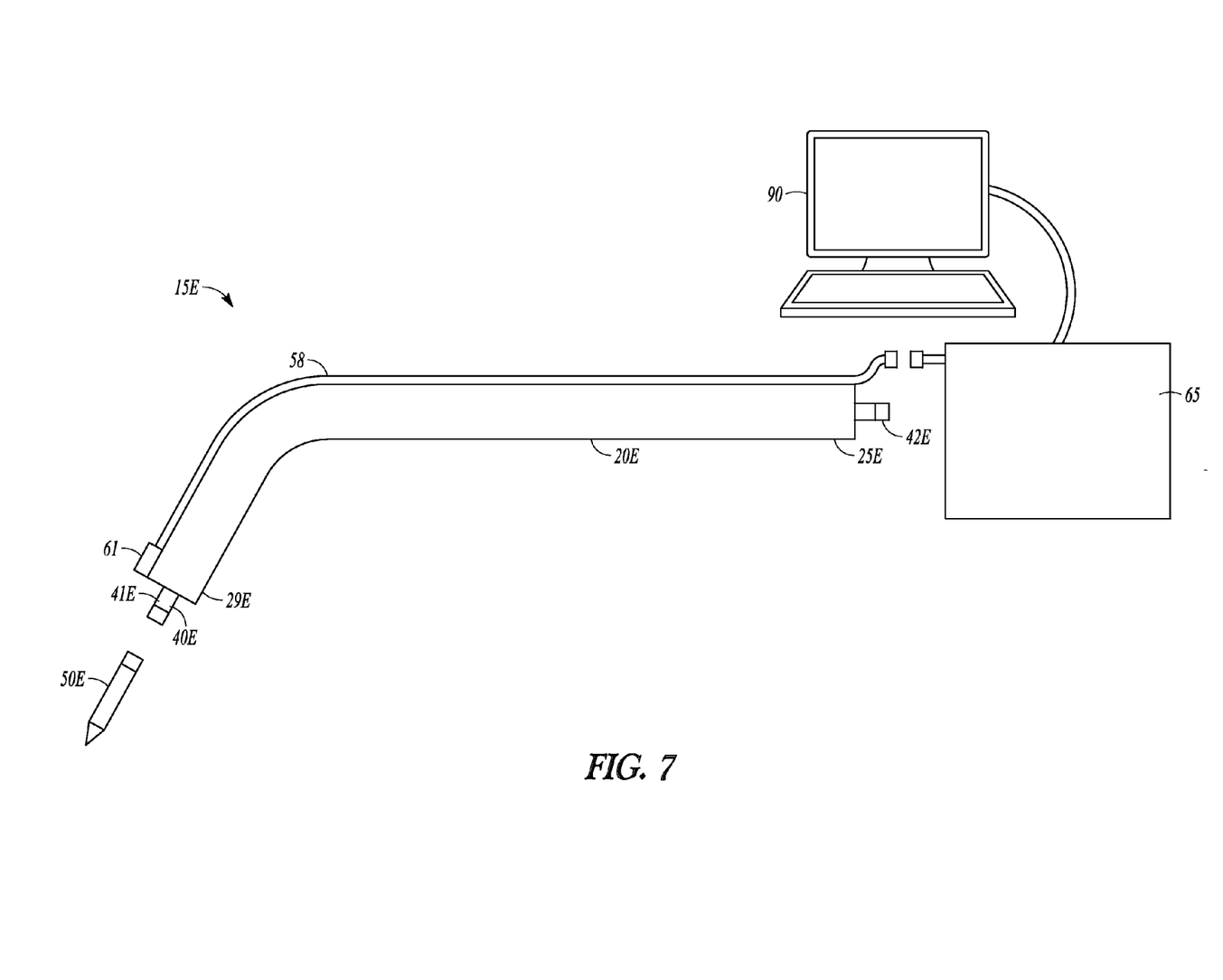
FIG. 7 illustrates a computer guided system, in accordance with at least one example of the present disclosure.

FIG. 7 illustrates a surgical tool 15E configured to be connected to a computer system 90, in accordance with at least one example of the present disclosure. The surgical tool 15E can include an outer guide tube 20E, an inner flexible shaft member 40E, and a shaft proximal end 42E configured to be connected to a driving device 65. The driving device 65 can be a manually operated device or a motorized device. A tube proximal end 25E can be connected to the driving device 65 for additional support. A guide tube cable 58 can extend from the tube proximal end 25E to a tube distal end 29E where it can connect to a multi-function unit 61. The multi-function unit 61 can employ one or more sensors and/or devices configured for depth control, location control, lighting, optics, recording, and working parameter (e.g. temperature, tip speed) measuring. In another example, the multifunction unit 61 can contain one or more transceivers for wirelessly transmitting and receiving information from a control unit. In another example, the functions of the multifunction unit 61 can be performed in a driven element 50E and wiring or optical fibers can be included in the inner portions of a cannula in the flexible shaft member 40E. The driven element 50E can include passages, spaces, or openings for wiring, optical fibers, flow passages, sensing devices, measuring devices or optical devices.

The connection to the computer system 90 can provide any computer associated functions such as monitoring, image display, and computer guided surgery. The tip of the flexible shaft member 40E can include a steering function. The steering function can include cables, wires, solenoids, or any steering method or device known to those skilled in the art. The steering function can direct the tip of the flexible shaft 40E or a steerable portion of the driven element 50E. In an example, the steering function can be configured to direct a drilling tip to seek a certain type of material, such as hard bone, and to avoid another type of material, such as soft cancellous bone. In another example, the drilling tip can be configured to remain within an intramedullary canal and avoid cutting into walls of cortical bone. Whether the steering of the driven element 50E or the tip of the flexible shaft member 40E manually controlled, automatically controlled, machine controlled, or self guided, the computer can display an image of tool tracking. This can be useful to, for example, aid in the placement of flexible implants, such as a zygomatic implant.

The depth control feature of the multi-function unit 61 can be configured as a spring loaded plunger that resides on the guide tube 20E. In an example where the surgical tool 15E is configured to drive an implant into bone, the plunger can measure displacement of the implant as it moves away from the tube distal end 29E. Depth control can be accomplished using any suitable component including, for example, a Hall Effect sensor, a liner potentiometer or any proximity sensor known to those skilled in the art. Advancement of the flexible shaft member 40E relative to the outer guide tube 20E can be measured at the tube distal end 29E or the tube proximal end 25E.

The driven element 50E can be configured as an integral portion of the shaft distal end 41E or as a connectable stand alone unit. In an example, the driven element 50E can be configured to harvest soft tissue or bone from locations such as the ramus of the mandible, the iliac crest, or the chin. In other examples, the driven element 50E can operate as a bone shaving tool in procedures such as a sinus lift. Furthermore, the flexible shaft member 40E and the outer guide tube 20E can be configured in any suitable shape or form that can provide the ability to reach difficult angles and locations necessary for a surgical operation such as a sinus lift or Schniderian membrane repair.

The driven element 50E and the flexible shaft member 40E can be cannulated. The driving device 65 can also include a lumen configured to allow the use of a guide wire during a surgical operation. The guide wire can be inserted into a surgical site, using radiography, computer aided tomography, or any other suitable imaging means. The proximal end of the guide wire can then be inserted into the distal end of the driven element 50E or the shaft distal end 41E (e.g. for a flexible shaft member with an integral tool on the tip. The guide wire can then pass through the flexible shaft member 40E and out a cannulated connection at the driving device 65. The flexible shaft member 40E can then follow the guide wire to the surgical site in preparation for a drilling operation.

Figure 8:
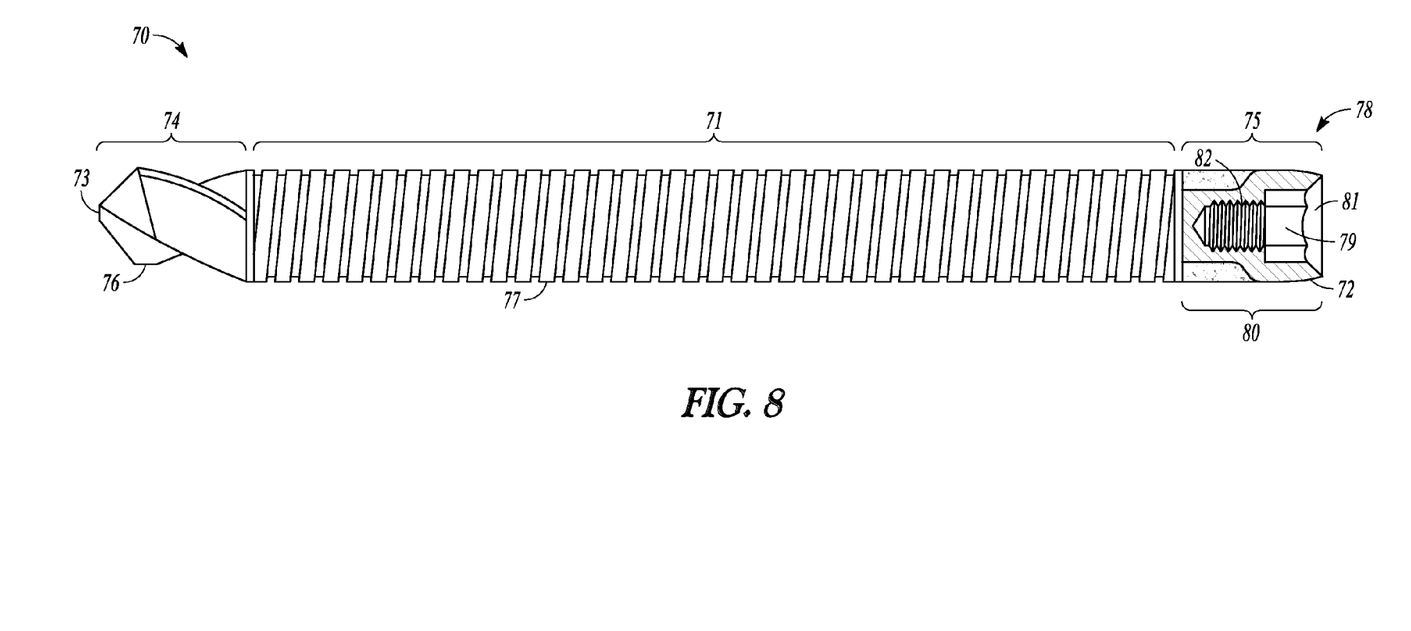
FIG. 8 illustrates a dental implant having a flexible shaft, in accordance with at least one example of the present disclosure.

FIG. 8 illustrates an example of a flexible implant 70. The flexible implant 70 can include flexible shaft member 71 extending from a proximal end 72 to a distal end 73, a cutting tip member 74 disposed on the distal end 73, and a proximal end connection 75. The cutting tip member 74 can be configured as a drill tip 76 as shown or a burr, a mill or any known configuration for advancing a tool into bone. The cutting tip member 74 can be configured to self-advance or "pull" the flexible implant 70 deeper into a bone site. The flexible implant 70 can be steerable or self-steering. The cutting tip member 74 can be configured to be steerable toward hard bone structure and to steer away from softer features such as the sinus cavities or the eye cavity. The cutting tip member 74 of the flexible implant 70 can be steerable by means of wires or cables controllable at the proximal end 72 of the flexible implant 70, or from other locations remote from the distal end 73. A surgeon can use guided surgery with a flexible implant 70 as outlined above and the flexible implant 70 can include fiber optic and/or electronic features to aid in placement and guidance.

The flexible shaft member 71 can be configured of a biocompatible material such as titanium, polymer, metal alloys, or combinations or materials. The flexible shaft member 71 can be made flexible in any suitable manner such configuring as a wire, a coil or a jointed structure, that can create or follow a curved pathway. The outer surface 77 of the flexible shaft member 71 can include a porous or semi porous material that can promote bone ingrowth. The outer surface 77 of the flexible implant 70 can be coated with bone morphogenetic proteins (BMPs), growth factors, antibiotics, probiotics or the like to promote bone growth and/or prevent infection. Inner portions of the flexible implant 70 can be cannulated and have additional features as described above. The proximal end connection 75 can be configured to be driven by a manual or motorized rotating device and can include connection features 78 such as a male or female hex fitting 79. The proximal end 72 can include a dental prosthetic connection 80 that can be configured to connect and secure a dental prosthetic, such as an abutment, a bridge or other such devices. The dental prosthetic connection 80 can include a conical taper 81 and/or a threaded internal aperture 82 configured to secure the dental prosthetic. The flexible implant 70 can be configured to be used with or without a guide tube 20 (see FIG. 3). The flexible implant 70 can be installed after a pilot hole or a final hole has been drilled into a surgical site or can be used to create the hole for its placement. Certain areas of the maxilla can include areas of low bone mass, such as regions underneath the sinus cavities of a human skull. The present inventors recognize that it can be beneficial to use a flexible implant 70 to create a curved pathway to areas of the skull having greater bone mass, such as the zygomatic arch region of the skull. The flexible implant 70 can include a diameter in the range of about 3 mm to about 6 mm. The flexible implant 70 can include a diameter in the range of about 2 mm to about 8 mm. The flexible implant 70 can include a diameter in the range of about 2 mm to about 6 mm. The flexible implant 70 can include a diameter in the range of about 2 mm to about 4 mm. The flexible implant 70 can include a diameter in the range of about 2 mm to about 3 mm. The flexible implant 70 can include a diameter in the range of about 4 mm to about 8 mm. The flexible implant 70 can include a diameter in the range of about 6 mm to about 8 mm.

The flexible implant 70 can include a length in the range of about 20 mm to about 50 mm. The flexible implant 70 can include a length in the range of about 10 mm to about 60 mm. The flexible implant 70 can include a length in the range of about 10 mm to about 50 mm. The flexible implant 70 can include a length in the range of about 10 mm to about 40 mm. The flexible implant 70 can include a length in the range of about 10 mm to about 30 mm. The flexible implant 70 can include a length in the range of about 10 mm to about 20 mm. The flexible implant 70 can include a length in the range of about 20 mm to about 60 mm. The flexible implant 70 can include a length in the range of about 30 mm to about 60 mm. The flexible implant 70 can include a length in the range of about 40 mm to about 60 mm. The flexible implant 70 can include a length in the range of about 50 mm to about 60 mm.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An implant system comprising:
   a dental implant comprising a first rotatable flexible shaft composed of a biocompatible material, the dental implant including an implant driving element positioned at a proximal end of the flexible shaft, the dental implant being configured for implantation into a portion of a skull of a patient;
   a second rotatable shaft including a cutting drill positioned at a distal end of the second flexible-shaft and a drill driving element positioned at a proximal end of the second shaft; and
   a surgical tool configured to be connected, in the alternative, to the drill driving element for forming a recessed surgical site and to the implant driving element for placing the dental implant in the recessed surgical site.

2. The implant system of claim 1, wherein the surgical site is formed in a zygomatic arch region of a human skull.

3. The implant system of claim 1, wherein the implant comprises a diameter between about 3 mm and about 6 mm and a length between about 20 mm and about 50 mm.

4. The implant system of claim 1, wherein the surgical tool comprises a flexible shaft.

5. The implant system of claim 1, wherein the implant driving element is comprises an opening configured to receive a dental prosthetic.

6. The implant system of claim 1, wherein the surgical tool further comprises an outer guide tube including a longitudinal body extending from a proximal end to a distal end of the body, wherein the outer guide tube includes at least one straight portion and at least one angled portion.

7. The implant system of claim 6, wherein the at least one angled portion is flexible.

8. The implant system of claim 6, wherein the surgical tool further comprises at least one of:
   a bearing positionable between the guide tube and the first rotatable flexible shaft or the second rotatable shaft; and
   a seal positionable between the guide tube and the first rotatable flexible shaft or the second rotatable shaft.

9. The dental implant system of claim 1, wherein a distal end of the dental implant is configured as a cutting tip.

10. The dental implant system of claim 1, wherein the first rotatable flexible shaft is bendable, such that the first rotatable flexible shaft is configured to take on a curved shape.

11. The dental implant system of claim 1, wherein the dental implant comprises a threaded internal aperture configured to engage with a threaded portion of a dental prosthetic, the dental prosthetic comprising an abutment.

* * * * *

UNITED STATES PATENT AND TRADEMARK OFFICE
CERTIFICATE OF CORRECTION

PATENT NO. : 9,744,008 B2
APPLICATION NO. : 14/270856
DATED : August 29, 2017
INVENTOR(S) : Bassett et al.

Page 1 of 1

It is certified that error appears in the above-identified patent and that said Letters Patent is hereby corrected as shown below:

In the Claims

In Column 16, Line 23, in Claim 1, delete "flexible-shaft" and insert --shaft-- therefor In Column 16, Line 39, in Claim 5, after "element", delete "is"

Signed and Sealed this
Twenty-eighth Day of May, 2019

Andrei Iancu
*Director of the United States Patent and Trademark Office*